United States Patent [19]
Friedman

[11] Patent Number: 6,129,686
[45] Date of Patent: Oct. 10, 2000

[54] PATIENT POSITION MONITOR

[76] Inventor: Mark B. Friedman, 5537 Darlington Rd., Pittsburgh, Pa. 15217

[21] Appl. No.: 09/324,548

[22] Filed: Jun. 3, 1999

Related U.S. Application Data

[62] Division of application No. 08/662,848, Jun. 12, 1996, Pat. No. 5,941,836.

[51] Int. Cl.[7] .............................. G01C 9/06; G08B 21/00; H01H 35/02
[52] U.S. Cl. .................................... 600/595; 200/DIG. 2; 200/61.45 R; 200/61.52; 340/573.1; 340/689
[58] Field of Search ...................... 600/595; 200/DIG. 2, 200/61.45 R, 61.52, 52 R; 340/573.1, 573.7, 689, 575, 573.4; 356/138, 139.1; 73/514.26

[56] References Cited

U.S. PATENT DOCUMENTS

| | | | |
|---|---|---|---|
| 3,163,856 | 12/1964 | Kirby | 340/279 |
| 4,348,562 | 9/1982 | Florin | 200/52 |
| 4,536,755 | 8/1985 | Holzgang et al. | 340/573 |
| 4,617,525 | 10/1986 | Lloyd | 340/573 |
| 5,038,137 | 8/1991 | Lloyd | 340/573 |
| 5,146,206 | 9/1992 | Callaway | 340/573 |
| 5,209,343 | 5/1993 | Romano et al. | 200/61.52 |
| 5,430,435 | 7/1995 | Hoch et al. | 340/573 |

*Primary Examiner*—John Mulcahy
*Attorney, Agent, or Firm*—Webb Ziesenheim Logsdon Orkin & Hanson, P.C.

[57] ABSTRACT

A patient position monitor is disclosed. The patient position monitor includes an inclinometer and a microprocessor connected to the output of the inclinometer. The inclinometer is a body axis orientation sensor having a light impermeable capsule including a cylindrical body. The longitudinal axis of the cylindrical body is parallel to the patient's body axis. The cylindrical body includes a first end portion having a circuit board with a radial array of sequentially illuminated LEDs. A light sensor is mounted on a second end portion of the cylindrical body. A light impermeable sphere disposed in the capsule between the array of LEDs and the light sensor is sized to block light emitted from a portion of the LEDs. The detection of light from the unblocked LEDs is indicative of the position of the sphere and of the orientation of the patient's body axis relative to gravity.

13 Claims, 6 Drawing Sheets

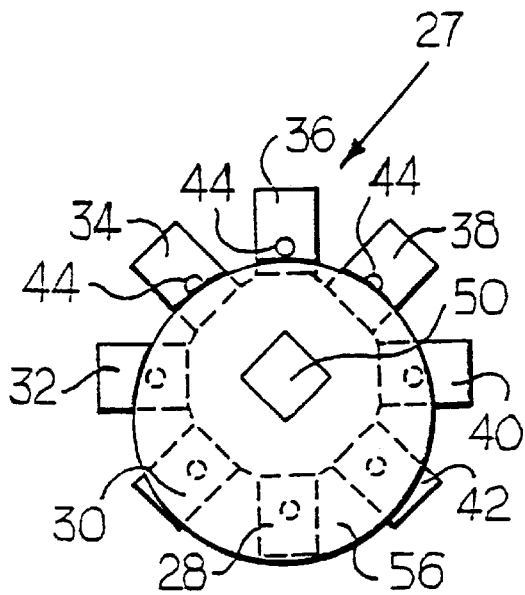
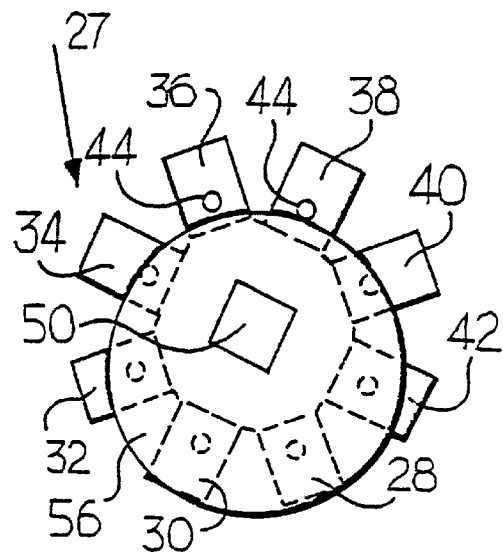
FIG. 4    FIG. 5
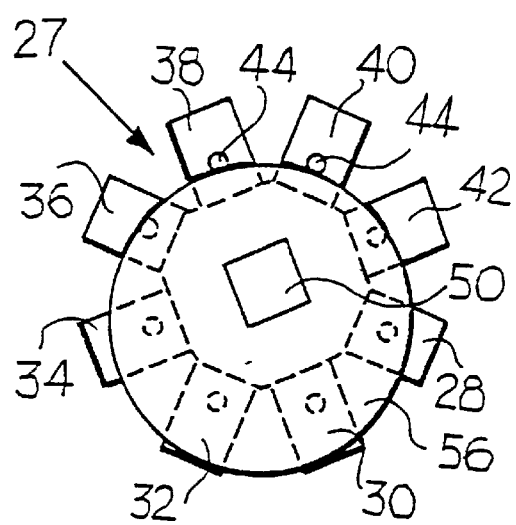
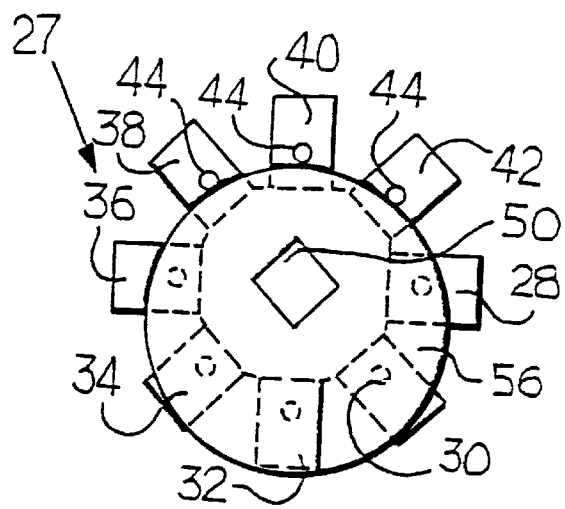
FIG. 6    FIG. 7

PATIENT POSITION MONITOR

RELATED APPLICATIONS

The present application is a divisional application of U.S. patent application Ser. No. 08/662,848, filed Jun. 12, 1996, entitled "Patient Position Monitor, now U.S. Pat. No. 5,941,836".

STATEMENT REGARDING FEDERALLY SPONSORED RESEARCH OR DEVELOPMENT

This invention was made with government support under grant numbers R43AG12626 and R44AG12626 awarded by the National institutes of Health. The government has certain rights in the invention.

BACKGROUND OF THE INVENTION

1. Field of the Invention

The present invention relates to a patient position monitor which senses and records the position and range of movement of a patient's body parts with respect to gravity.

2. Description of the Prior Art

Bed bound patients, such as those in nursing homes and other long-term care facilities, who are too ill or too weak to roll over in bed frequently get pressure ulcers from the occlusion of blood flow caused by pressure compressing soft tissues between bony prominences and the bed. Once formed, pressure ulcers are expensive to heal. Pressure ulcers can be prevented by regular turning of the patient in bed to relieve pressure from the compressed tissue. A turning intervention program by caregivers may be prescribed. Typical turning intervention programs call for repositioning the patient every two hours around the clock.

Although turning intervention programs often are prescribed to periodically relieve pressure of compressed tissues, they are not always successful for a variety of reasons. Turning interventions may be delayed or omitted because of situational exigencies or due to a lack of understanding by nursing staff of the clinical consequences of missed or delayed interventions.

Patients who are confined to a bed are not necessarily completely immobile. Some such patients spontaneously turn themselves, but self-turning is not predictable or regular, thus self-turners also require intervention during some parts of the day. Moreover, it is difficult, if not impossible, for the nursing staff to determine when a patient last spontaneously turned. Patient records are not maintained on such spontaneous turning even if they are known to occur. In other circumstances, the nursing staff will turn a patient and the patient at some point will subsequently turn back to the original more comfortable position, making the pressure relieving turn ineffective.

Turning intervention programs are prescribed for around the clock turnings, thus patients usually awake from night-time sleep when being turned. Some patients who do receive turning intervention may be turning on their own and thus, their sleep is unnecessarily disturbed by nursing staff complying with the prescribed turning intervention during the night.

Even when written turning intervention schedules are prescribed, a combination of caregivers' lack of perception of the consequences of missed interventions, inadequate patient risk assessment tools to determine who truly needs turning intervention and flawed nursing care management practices together account for the failure of such intervention programs to minimize the development of pressure ulcers of mobility impaired residents of nursing care facilities.

Another aspect of the mobilization of patients living in long-term care facilities is the frequency and duration that the patients stand or walk each day. Because some patients require physical restraints for medical reasons or to ensure their physical safety, they may be forced to remain in chairs by use of belts, vests, jackets, trays, bars, and the like. Once restrained, oftentimes these patients are not freed to stand or move for long periods of time either because it is difficult for the nursing staff to know when a patient was last moved or simply due to nursing staff convenience or neglect. According to current health care practice, patients restrained in a seated position should be permitted to or assisted to stand or walk for at least 10 minutes every two hours.

Devices which detect the movement of a person by a prescribed degree have been described previously. For example, a device which monitors the sleep posture of a patient and provides an alarm for generating a stimulus to awaken the person if movement has not been detected from that particular posture in a prescribed amount of time is disclosed in U.S. Pat. No. 4,617,525. The sleep posture monitor includes a position sensor capable of detecting movement from a single position. Neither the position of the patient relative to gravity nor the subsequent positions are recorded.

A similar device is disclosed in U.S. Pat. No. 3,163,856. A wrist-worn motion detector is used to determine whether a person has not moved within a given period of time. In one embodiment, the wrist-worn motion detector comprises a conductive ball contained in an annular raceway which connects adjacent pairs of electrodes. Motion by the patient causes the ball to roll about the raceway to make and break adjacent pairs of contacts. An alarm is sounded if no movement is detected for a certain period of time. This motion sensor detects movement by a patient, but there is no indication of the direction of movement and actual position of the patient or the duration of time spent in each position.

A patient position monitor which detects the change in the angle of position of a patient such as occurs when a patient has fallen from a bed or chair or the like is disclosed in U.S. Pat. No. 4,348,562. A mercury switch is secured to a patient to detect when the patient has moved from a horizontal to vertical position. The mercury switch comprises a two-chambered body where the chambers are connected by a passageway having a slope through which a ball of mercury can only pass from a first chamber to a second chamber (which contains electrodes) when the patient has moved from a horizontal to a vertical position to an angle beyond 40 to 70 degrees. An electrical circuit is completed only when the patient raises sufficiently from a horizontal position for the ball to enter the second chamber and close the circuit.

An apparatus for monitoring patient activity comprising an angle inclination sensing means mounted to a patient's legs is disclosed in U.S. Pat. No. 4,536,755. The sensing means comprises a mercury switch which is actuated when the switch is oriented in a downward position when the patient is standing vertically. Contact of the mercury with two electrodes occurs whenever a predetermined inclination threshold angle is exceeded.

Neither of these devices monitor the rotation of the patient's torso and its position relative to gravity. They provide information only when the patient moves beyond a predetermined position and do not monitor the time spent in a particular position.

Despite these advances in patient position monitoring, a need remains for a patient position monitor which detects the duration of each position assumed by a patient reclining in bed relative to gravity and provides data on the past positions of the patient relative to gravity along with the degree of change of the patient's position and duration of time in each position to diagnose the need for turning intervention programs and to assist nursing staff in the implementation of turning intervention programs. A need also remains for a patient position monitor which detects the movement of a patient from a horizontal to a vertical position and the duration of time in each position.

SUMMARY OF THE INVENTION

This need is met by the patient position monitor of the present invention which monitors the orientation of a part of a patient's body with respect to gravity. The patient position monitor includes means for repeatedly measuring the orientation of a part of a patient's body with respect to gravity and means for determining the length of time spent in that orientation. The means for repeatedly measuring orientation preferably is an inclinometer and the means for determining the length of time spent in that orientation preferably is a microprocessor which receives output from the inclinometer. The inclinometer and microprocessor preferably are housed together in a single unit and attached to a patient by a strap or band or the like.

The patient position monitor of the present repeatedly samples the orientation with respect to gravity of the patient's body axis. It may also be used to detect changes in the verticality of the patient. Output from the microprocessor may be stored or transmitted to a remote receiver for display.

The inclinometer includes a body axis orientation sensor having a cylindrical body with a first end portion and a second end portion. The longitudinal axis of the cylindrical body is parallel to the patient's body axis. The first end portion includes a circuit board having a radial array of illuminated light emitting diodes (LEDs). A light sensor is mounted on the second end position of the capsule. A light impermeable sphere is disposed in the capsule between the array of LEDs and the light sensor. The sphere is sized to block light from a portion of the LEDs. The sphere falls by gravity and blocks a portion of the array depending on the orientation of the patient's body axis. The detection by the light sensor of light emitted from the LEDs and not blocked by the sphere is indicative of the position of the sphere relative to gravity and of the orientation of the patient's body axis relative to gravity.

Preferably, the array of LEDs includes eight LEDs and light emitted from five or six of the LEDs is blocked by the sphere. The light sensor preferably is a phototransistor. In an alternative embodiment, the second end portion of the capsule includes a sphere retainer wherein when the longitudinal axis of the cylindrical body is vertical or nearly vertical, the sphere is restrained within the sphere retainer such that the sphere blocks either all or none of the light emitted from the LEDs from reaching the phototransistor. Preferably, the sphere retainer is a tapered wall of the cylindrical body. The angle formed between the tapered wall and the wall of the body of the capsule preferably is about 120 to 135 degrees, ore preferably about 120 degrees.

Each LED preferably is sequentially illuminated for 0.5 msec every 15 seconds. By using eight LEDs, the inclinometer detects rotation of the longitudinal axis of the patient of about 22.5 degrees.

The inclinometer may also be a verticality sensor. The components of the verticality sensor are similar to those of the body axis orientation sensor except that the longitudinal axis of the cylindrical body is orthogonal to the patient's body axis and is positioned medially-laterally on the patient. When worn on the ventral surface of a patient's thigh and the patient moves from a supine or seated position to standing or walking, the sphere falls by gravity within the housing and blocks light from a portion of the LEDs in a manner similar to that of the body axis orientation sensor.

The patient position monitor may include a plurality of inclinometers having components similar to the body axis orientation sensor wherein each of the longitudinal axis of each cylindrical body of each inclinometer is orthogonal to one another.

In another embodiment, the longitudinal body axis position sensor or vertical movement sensor includes a wire cage and conductive ball inclinometer. The wire cage and conductive ball inclinometer includes a nonconductive housing and a conductive sphere surrounded by a plurality of wires disposed parallel to the body axis of the patient and arranged in a circle within the housing. The wires include an even-numbered plurality of output wires and a same number of input wires. Each output wire is separated from each other by an input wire. A plurality of input leads connects each input wire to a microprocessor. Every other output wire is connected to one of a pair of output leads. The other output wires are connected to the other of the output leads.

The conductive ball is sized to contact one of the output wires and one of the input wires adjacent the one output wire. The location of the contact is indicative of the position of the conductive ball within the wire cage relative to gravity.

When strapped to a patient's torso or thigh so that the wires are parallel to the patient's spinal axis, the position of the conductive ball relative to gravity is indicative of the orientation of the patient's body axis relative to gravity.

The longitudinal body axis orientation sensor or the verticality sensor may be an accelerometer.

The present invention also includes a method of monitoring the orientations of the longitudinal body axis of a patient lying down having the steps of: (a) attaching a patient position monitor to the torso or thigh of a patient, the patient position monitor comprising a body axis orientation sensor and a microprocessor which receives output from the body axis orientation sensor; (b) repeatedly measuring the orientation of the body axis of the patient with respect to gravity; and (c) measuring the time spent in the orientation measured in step (b). changes in the orientation of the patient's body axis may be accomplished by the patient or with assistance from another person. The body axis orientation sensor preferably is one of the above described embodiments thereof.

The present invention further includes a method of preventing pressure ulcers in a bed bound patient including performing the above-described steps of the method of monitoring the orientations of the body axis of a patient further including rotating the body axis of the patient within a prescribed repositioning time period such that the time measured in step (c) is within the prescribed repositioning period.

The present invention also includes a method of monitoring the verticality of a patient having the steps of: (a) attaching a patient position monitor to the thigh of a patient, the patient position monitor comprising a verticality sensor and a microprocessor which receives output from the verticality sensor; (b) repeatedly measuring the orientation of the patient's thigh relative to vertical; and (c) measuring the time spent in the orientation measured in step (b). The verticality sensor employed in this method preferably is the above-described inventive verticality sensor.

The present invention further includes a method of determining compliance with a patient repositioning regimen having the steps of: (a) attaching a patient position monitor to a body part of a patient, the patient position monitor comprising an inclinometer, a microprocessor which receives output from the inclinometer and a recorder which records data from the microprocessor; (b) repeatedly measuring the orientation of the body part of the patient relative to gravity; (c) measuring the time spent in the orientations; (d) recording the measurements of the orientations of the body part of the patient relative to gravity and the time spent in the orientation; and (e) comparing the measurements recorded in step (d) to orientation and time parameters of a prescribed repositioning regimen. An alarm may be sounded when the measurements compared in step (e) do not conform with the parameters of the prescribed repositioning regimen. The method may further include a step of transmitting the measurements recorded in step (d) to a remote receiver which may display the measurements recorded in step (d).

The present invention also includes a method of diagnosing a patient's need for a repositioning regimen comprising the steps of: (a) attaching a patient position monitor to a body part of a patient, the patient position monitor comprising an inclinometer, a microprocessor which receives output from the inclinometer and a recorder which records data from the microprocessor; (b) repeatedly measuring the orientation of the body part of the patient relative to gravity; (c) measuring the time spent in the orientations; (d) recording the measurements of the orientations of the body part of the patient relative to gravity and the time spent in the orientation; and (e) comparing the measurements recorded in step (d) to a set of predetermined minimal repositioning orientation and time parameters.

BRIEF DESCRIPTION OF THE DRAWINGS

FIG. 4 is a sectional view of the patient position monitor through line IV—IV of FIG. 3 when a patient is in the supine position only showing the light impermeable sphere and LEDs and the axial position of the phototransistor;

FIG. 5 is a view of the sphere and LED array of FIG. 4 when the patient has rolled 22.5 degrees counterclockwise from the supine position;

FIG. 6 is a view of the sphere and LED array of FIG. 4 when the patient has rolled 67.5 degrees counterclockwise from the supine position;

FIG. 7 is a front view of the sphere and LED array of FIG. 4 when the patient has rolled 90 degrees counterclockwise from the supine position;

DESCRIPTION OF THE PREFERRED EMBODIMENTS

The present invention includes a patient position monitor for detecting the orientation of a part of a patient's body relative to gravity.

Figure 1:
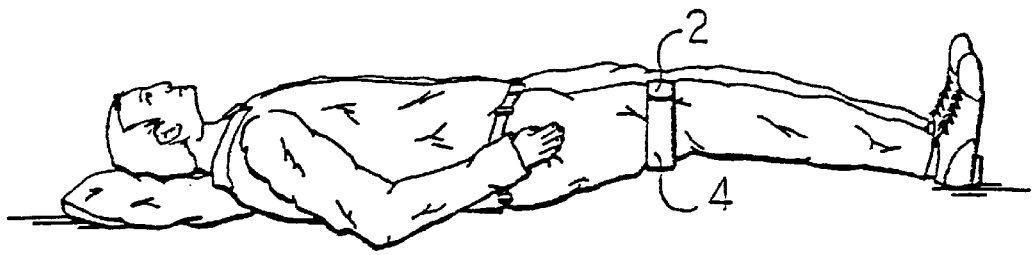
FIG. 1 is a side view of a patient lying in bed wearing the patient position monitor of the present invention.

One embodiment of the patient position monitor of the present invention is illustrated in FIGS. 1–8. The patient position monitor 2 is mounted on the ventral thigh or torso of a patient in the supine position as shown in FIG. 1.

The patient position monitor preferably is worn on the thigh or lower torso. Placement near the ankle is not preferred because lower leg mobility does not necessarily reflect torso or thigh position. The patient position monitor is retained on the thigh or torso by a strap 4 or the like.

In its most basic form, the inventive patient position monitor includes means for repeatedly measuring the orientation of a part of a patient's body with respect to gravity and means for determining the length of time the part of the patient's body spends in the orientation.

Figure 2:
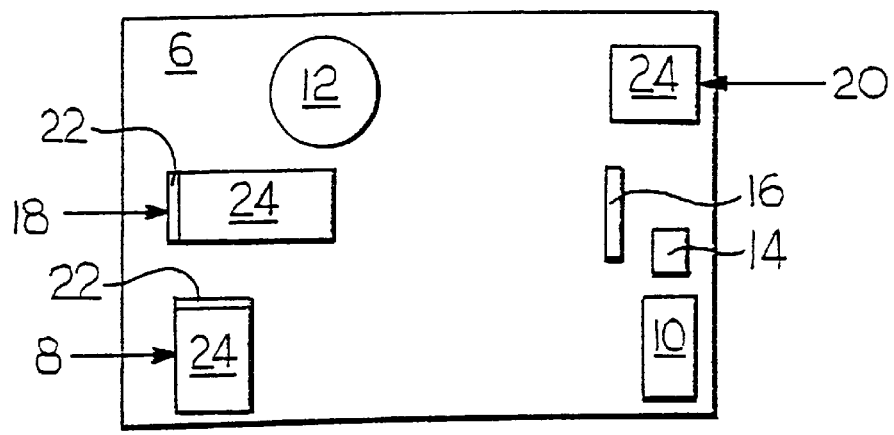
FIG. 2 is a schematic plan view of the patient position monitor.

The patient position monitor depicted schematically in FIG. 2 (without connections between the components) includes, mounted on mother board 6, a body axis orientation sensor 8, a microprocessor 10 and a power source or battery 12. In the preferred embodiment, the patient position monitor includes a memory device 14, time keeper crystal 16 and a verticality sensor 18. The patient position monitor may also include a third sensor 20. These components are electrically connected via the mother board 6 in accordance with conventional electronics practice. The three sensors 8, 18 and 20 are positioned on the mother board 6 orthogonal to each other. Sensors 8, 18 and 20 are similar, thus the details of sensor 8, described below, apply to each of sensors 18 and 20.

Figure 3:
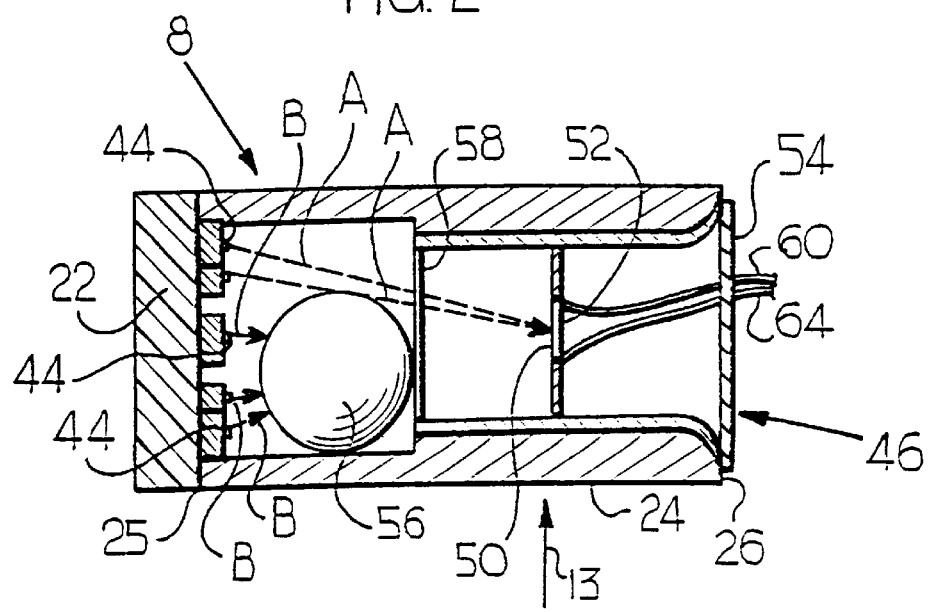
FIG. 3 is a sectional elevation view of the body axis orientation sensor of the present invention.

As depicted in FIG. 3, body axis orientation sensor 8 includes an LED board 22 and a light impermeable capsule 23. The capsule 23 includes a body 24 including a wall thereof, preferably cylindrical in shape and having a longitudinal axis, and a first end portion 25 and a second end portion 26. When the body axis orientation sensor 8 is worn by a patient, the longitudinal axis of the cylindrical body is placed parallel to the patient's body axis. By the phrase "body axis" it is meant the axis of the patient's body extending between the rostral and caudal ends of the patient. The LED board 22 is fixed to the first end portion 25 of the capsule 24 and preferably is disposed in a plane orthogonal to the plane of mother board 6. LED board 22 supports an array 27 of eight radially arranged (as in the spokes of a wheel) light emitting diodes (LEDs) 28, 30, 32, 34, 36, 38, 40 and 42 each having a light source 44. The LEDs are powered by the battery 12 via microprocessor output leads. Each LED preferably is illuminated for about 0.5 msec, one at a time in a clockwise sequence beginning with first LED 28, immediately followed by second LED 30, third LED 32, fourth LED 34, fifth LED 36, sixth LED 38, seventh LED 40 and eighth LED 42. During the LED lighting sequence, the complete array 27 of LEDs preferably is illuminated for about 4 msec every 15 seconds which minimizes the duty cycle and maximizes the life of the battery.

A light sensor 46 is tightly housed with the capsule 23. Light sensor 46 preferably includes a phototransistor 50 mounted on a central wall 52 in the light sensor 46 in a plane parallel to the plane of the LED board 22. One end wall 54 of light sensor 46 preferably is flared to seat the end wall 54 on second end portion 26. Light emitted from the array of LEDs 27 is receivable by phototransistor 50. The other end wall 58 of light sensor 46 is light transmissive and preferably is made of glass.

A light impermeable sphere 56 is positioned within the capsule 23 between the array of LEDs 27 and the light transmissive end wall 58. The sphere 56 is sized sufficiently small so that it is free to move inside the capsule 24 yet sufficiently large that at any given position of the sphere 56, the sphere 56 blocks light emitted from all but 2 or 3 of the LEDs from reaching phototransistor 50. Typically, the sphere is about 1/8 inch in diameter and the capsule is 3/16 inch in diameter. Thus, the light sensor 46 detects light emitted from only 2 or 3 of the LEDs in each lighting sequence as depicted by arrow lines A in FIG. 3. Arrow lines B depict light from LEDs which is blocked by the sphere 56. The light transmissive end wall 58 prevents the sphere 56 from contacting the phototransistor 50. Phototransistor 50 is connected to microprocessor 10 via leads 60.

Figure 8A:
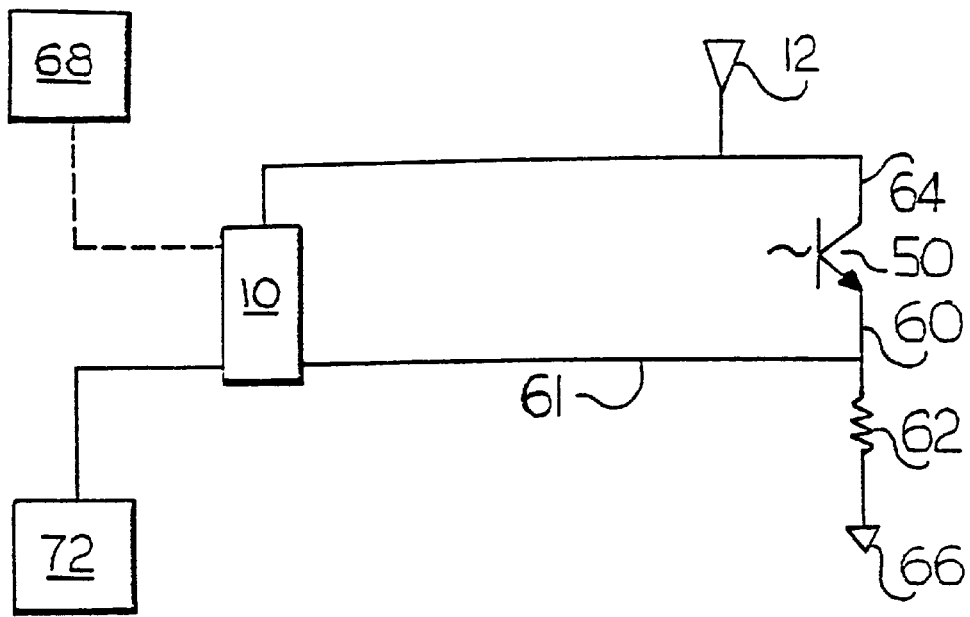
FIG. 8A is a schematic circuit diagram of the patient position monitor.

As shown schematically in FIG. 8A, the phototransistor 50 provides low resistance (preferably less than 1 KΩ) when it receives light from an LED and provides high resistance (preferably about 1000 KΩ) when no light is received. A middle resistance resistor, preferably about 100 KΩ, placed in series with the phototransistor 50 connects a positive lead 64 (at $^+$V) from power supply 12 to ground 66. Thus, when light is detected by light sensor 46, the input 61 to microprocessor 10 is high (99% of $^+$V). When no light is detected by light sensor 46, the input to microprocessor 10 is low (10% of $^+$V). Preferably, the digital threshold of microprocessor 10 is set at about 50% $^+$V.

When the patient position monitor 2 is worn by a supine patient, the sphere 56 falls by gravity and blocks light emitted from the first, second, third, seventh and eighth LEDs 28, 30, 32, 40 and 42, respectively, as depicted in FIG. 4. The microprocessor 10 receives high signal input for the fourth, fifth and sixth LEDs 34, 36 and 38, respectively, and low signal input from phototransistor 50 for the remaining LEDs after each LED is illuminated. A high input from the phototransistor 50 after LEDs 24, 26 and 28 are each illuminated is interpreted by the microprocessor as zero degrees or that the patient is supine.

When the patient rolls or is turned 22.5 degrees counterclockwise, the capsule 24 rotates accordingly so that the sphere 56 falls by gravity and blocks light from all but fifth LED 36 and sixth LED 38 as shown in FIG. 5. Upon further rotation of the patient to 67.5 degrees counterclockwise, light from only sixth LED 38 and seventh LED 40 may be detected as shown in FIG. 6. When the patient has rolled to his or her side, i.e., 90 degrees counterclockwise, light from the sixth, seventh and eighth LEDs 38, 40 and 42 may be detected as shown in FIG. 7. Rolling or turning of the patient in the clockwise direction allows for detection of body axis position relative to gravity at 22.5, 67.5 and 90 clockwise degrees in a similar manner.

When the ball blocks the direct path of light from an LED to the phototransistor 50, the microprocessor input remains unasserted or is read as "0". When the sphere 56 does not block the light path from the LED to the phototransistor 50, the microprocessor input is asserted by the phototransistor 50 or is read as "1". When one illuminating sequence of the eight LEDs is completed, a digital word is assembled in a register of the microprocessor. The digital word is compared to a reference table in the microprocessor to determine the light sensor's orientation with respect to gravity.

For example, the digital word "00011100" is assembled when the patient is in the supine position (FIG. 3) and light is detected from LEDs 34, 36 and 38 only. Upon rotation of 90° counterclockwise (FIG. 7), light is detected only from LEDs 38, 40 and 42 which results in the assembly of the digital word "00000111".

The body axis rotation sensor can be made more or less sensitive to changes in the orientation of the patient's body axis by using more or less LEDs respectively. For the purposes of preventing pressure ulcers through a monitoring system, detection of changes in position of 22.5 degrees is sufficient.

Measurements of the patient's body axis orientation with respect to gravity are regularly and repeatedly taken by illuminating the array 27 of LEDs over a period of time. The frequency that the measurements are taken and duration of the measurement period depends on the particular application of the inventive patient position monitor and can range from a few minutes to several hours or longer. A change in the orientation of the patient's body axis is detected when the measurements taken by the body axis orientation sensor indicates that light from a different set of LEDs has been detected by the phototransistor 50. The length of time that the patient's body axis was in a particular orientation is determined by measuring the length of time between the time when the last orientation measurement at one orientation was taken and the later time when another orientation measurement at another orientation was taken.

The duty cycle of the battery may be reduced in the following manner. The array of LEDs is sequentially illuminated until the phototransistor 50 detects a lit LED.

The next LEDs in the array are sequentially illuminated until the phototransistor 50 first fails to detect light from an LED because the sphere blocks this LED. The remaining LEDS in the array 27, which must also be blocked, are not illuminated to conserve power. The next time the array 27 is to be sequentially illuminated, only the 4 or 5 LEDs around the expected unblocked LEDs are illuminated.

Figures 12A, 12B:
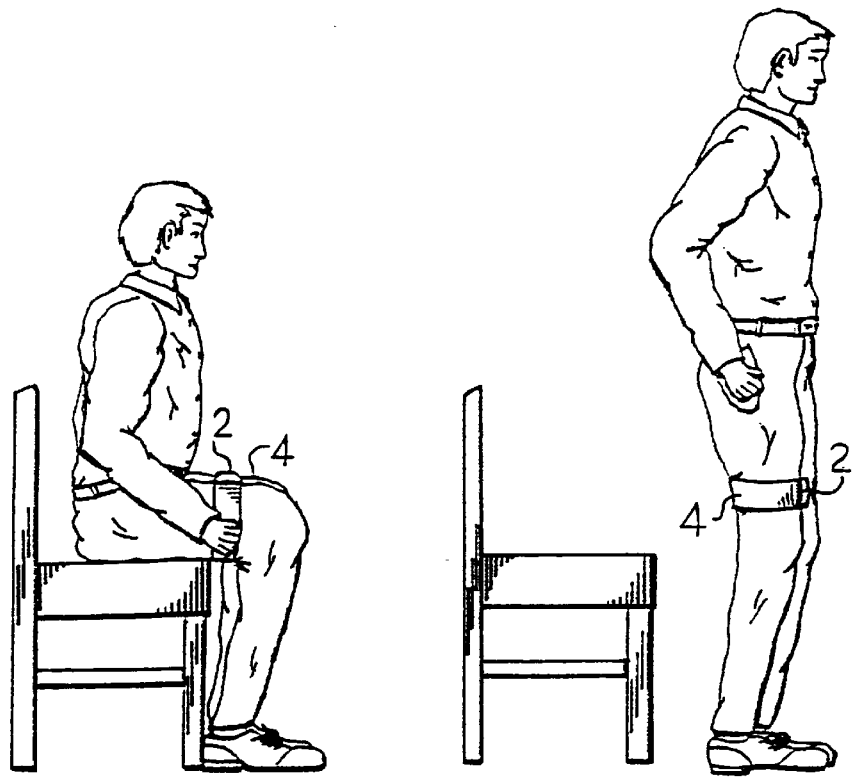
FIG. 12A is a side view of a patient wearing the claimed patient verticality sensor when seated.
FIG. 12B is a side view of a patient wearing the claimed patient verticality sensor when standing.

As depicted in FIG. 2, the patient position monitor of the present invention includes a body axis orientation sensor 8 and preferably includes a verticality sensor 18 and may include a third sensor 20. When the patient position monitor includes verticality sensor 18, it can be used as a vertical movement monitor to detect movement of a patient from a seated or supine position to a vertical position such as in standing or walking as shown in FIGS. 12A and 12B. When the device is used to measure orientation of the body axis of a patient, the longitudinal axis of the cylindrical body 24 of the body axis position sensor 8 is parallel to the patient's body axis. When the device is used to measure the orientation of a patient's thigh relative to vertical, the longitudinal axis of the cylindrical body 24 is orthogonal to the patient's thigh axis and disposed medially-laterally to the patient. By the phrase "thigh axis" it is meant the longitudinal axis of the patient's thigh extending between the hip and knee. When the patient moves from a seated position to standing or walking, the sphere 56 falls by gravity to block all but two or three of the LEDs in a similar fashion as described above with reference to FIGS. 4–7.

Some patients tend to disturb monitoring devices attached to their bodies. In particular, it is possible for a patient to move the strap 4 about the thigh so that the longitudinal axis of the cylindrical body 24 of the verticality sensor 18 is no longer disposed medially-laterally to the patient. In these instances, the third sensor 20 may be used. Detection of the position of each sensor 8, 18 and 20 relative to gravity provides complete information on the position of the patient.

Figure 13:
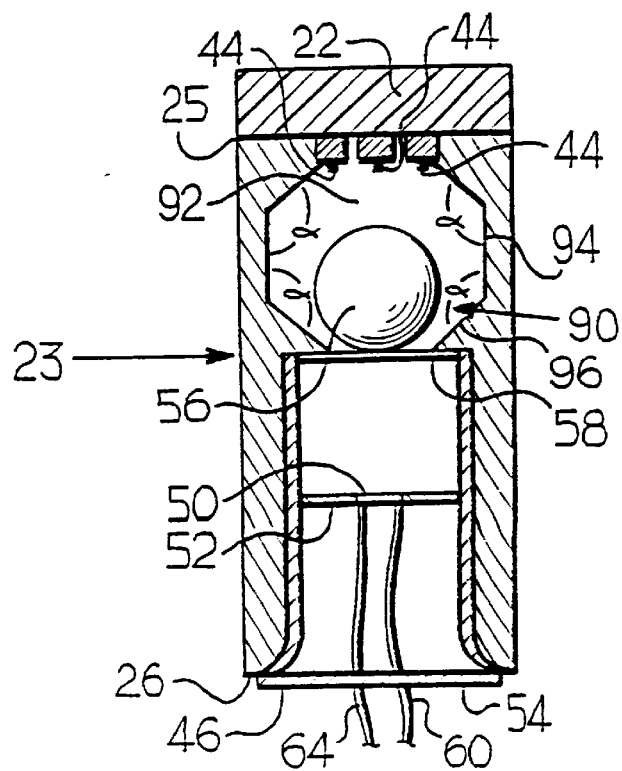
FIG. 13 is a sectional elevation view of an alternative embodiment of the body axis orientation sensor in a vertical or near vertical orientation.

The verticality sensor 18 and third sensor 20 may be eliminated by the following alternative embodiment. As shown in FIG. 13, first end portion 25 of the cylindrical body 24 of the body axis orientation sensor 8 includes a sphere retainer 90. Preferably, sphere retainer 90 includes a first tapered wall 92. Side wall 94 is disposed between first tapered wall 92 and a second tapered wall 96. Each of first tapered wall 92 and second tapered wall 96 form an angle a with side wall 94. Angle α is about 120 to 135 degrees, preferably about 120 degrees.

During use in a patient position monitor on a patient's thigh, the sphere 56 of the body axis orientation sensor 8 will fall into the funnel shape created by the confines of second tapered wall 96 when the patient's thigh becomes vertical or nearly vertical such as when the patient stands. In effect, the sphere 56 becomes restrained within the confines of second tapered wall 96 and blocks all light emitted from the LEDs from reaching the phototransistor 50. Likewise, if somehow the patient's thigh becomes so vertical that the sphere 56 becomes restrained within the confines of first tapered wall 92, the sphere 56 blocks light emitted from all of the LEDs from reaching the phototransistor 50. When the microprocessor 10 receives no input from the phototransistor 50, the patient's thigh must be vertical or nearly vertical.

When the patient is supine, the body axis orientation sensor 8 operates as described in the previous embodiment. However, when the patient's thigh becomes vertical, the microprocessor 10 will interpret the absence of any signal from the phototransistor 50 as meaning that the capsule 23 has become sufficiently vertical to cause the sphere 56 to be restrained within the confines of either first tapered wall 92 or second tapered wall 96, i.e., that the patient's thigh is vertical. Thus, a single sensor may be used to measure orientation of the patient's body axis with respect to gravity and to measure verticality of the patient's thigh.

Alternatively, the tapered walls 92 and 96 may be light transmissive and the sphere 56 is sized sufficiently small such when the patient's thigh becomes vertical or nearly vertical, the sphere 56 becomes restrained within the confines of the tapered walls 92 and 96 and light from all the LEDs passes the sphere 56 and is detected by the phototransistor 50. Thus, when the microprocessor 10 receives input from the phototransistor 50 that light from all the LEDs was received, the patient's thigh must be vertical or nearly vertical.

The verticality sensor 18 may also be used to detect fine movements (less than 22.5°) of a patient's thigh relative to gravity without using additional LEDs in the array 27. When the patient position monitor 2 is strapped to an ambulatory patient's thigh, the sphere 56 moves back and forth within the capsule 23 of the verticality sensor 18. The change in verticality of the ambulatory patient's thigh may be as small as 2 to 3 degrees. Small changes in the position of an ambulatory patient's thigh are most common in the shuffling gait of feeble individuals.

Figure 9A:
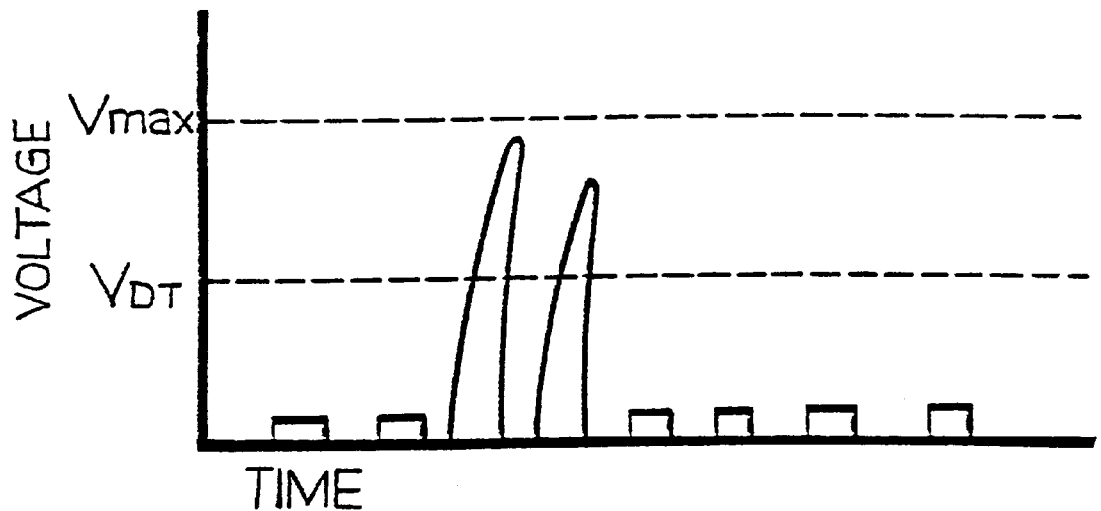
FIG. 9A is a graph of voltage over time from the phototransistor of an alternative embodiment of the present invention.
Figure 9B:
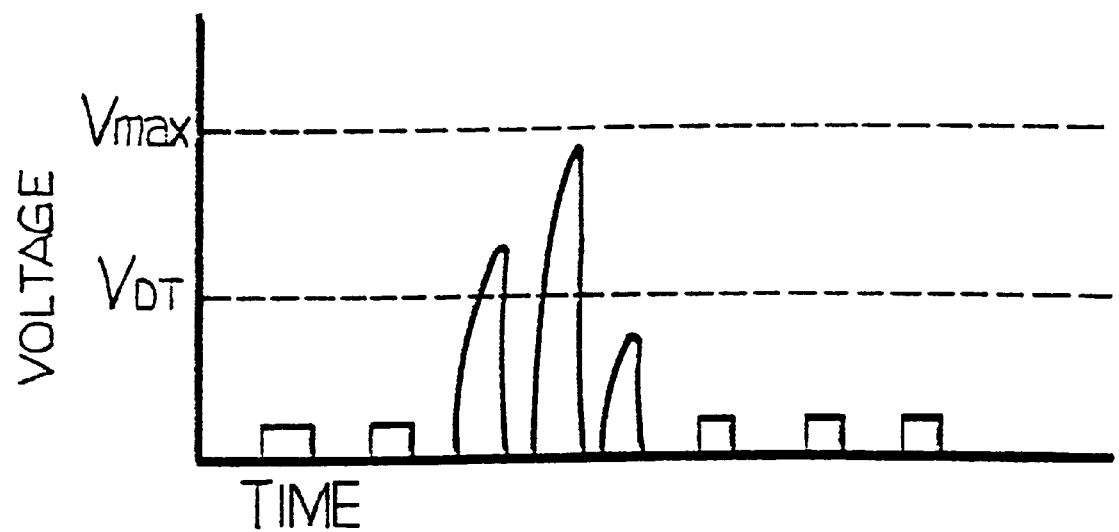
FIG. 9B is a graph of voltage over time from the phototransistor after the patient has moved slightly.

When used to detect fine movements, ratiometric sensing is employed. By the phrase "ratiometric sensing" it is meant that the relative strengths of signals from a sensor are compared. For example, when light emitted from third LED 32 and fourth LED 34 is detectable by the phototransistor 50, the signal received from the phototransistor 50 is as depicted in FIG. 9A. As the patient's thigh moves about 10 degrees, light is detected from third LED 32, fourth LED 34 but does not produce a signal higher than the digital threshold ($V_{dt}$) from fifth LED 36 and decreasing signal from third LED 32. An analog to digital converter may be included in microprocessor 10 in order to view the increasing signal due to light detected from fifth LED 36.

Figure 8B:
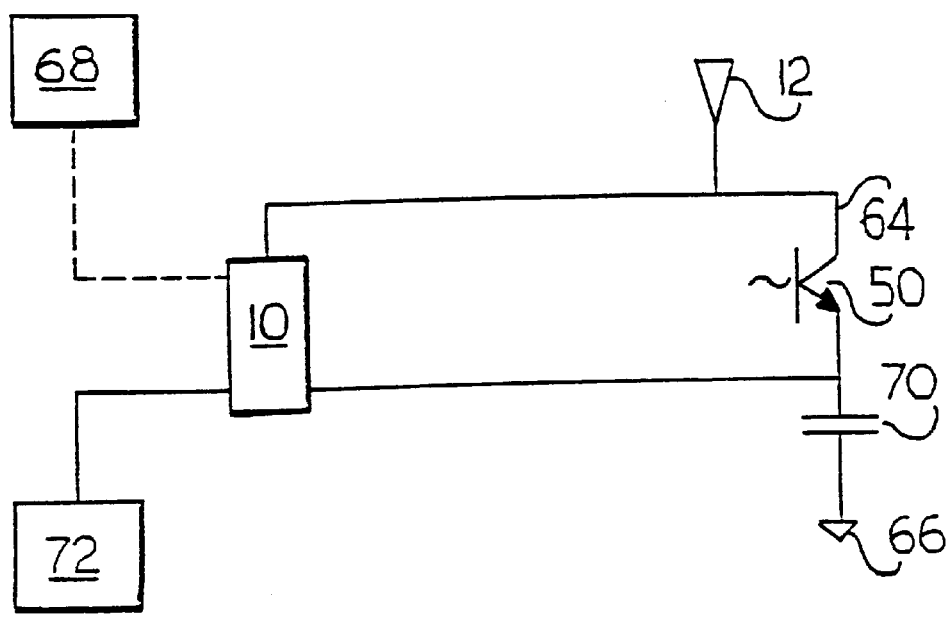
FIG. 8B is a schematic circuit diagram of an alternative embodiment of the patient position monitor.

Alternatively, a circuit as depicted in FIG. 8B is used wherein resistor 62 is replaced with a capacitor 70. This arrangement avoids the use of an expensive analog to digital convertor. The microprocessor 10 detects the amount of time it takes for the capacitor 70 to accumulate charge and reach or surpass the digital threshold for each LED in the illumination sequence. A timer within the microprocessor 10 is preset to dump charge accumulated on the capacitor 70 after a certain period of time. If the digital threshold is not reached within the preset time period, the microprocessor interprets this state as indicating that the LED is blocked by the sphere 56. The time it takes for the charge to accumulate on the capacitor 70 above the digital threshold is indicative of the amount of light from an LED that reaches the phototransistor 50. The relative time it takes for the charge collected to exceed digital threshold from adjacent LEDs is interpreted by the microprocessor 10 to determine the position of the sphere 56 and in turn, the position of the patient relative to gravity.

The number of LEDs can be reduced to three or four when the circuit depicted in FIG. 8B is used with ratiometric sensing. Three LEDs are sufficient to define rotational orientation in the plane of the array. Four LEDs provide redundancy in the array.

Figure 10:
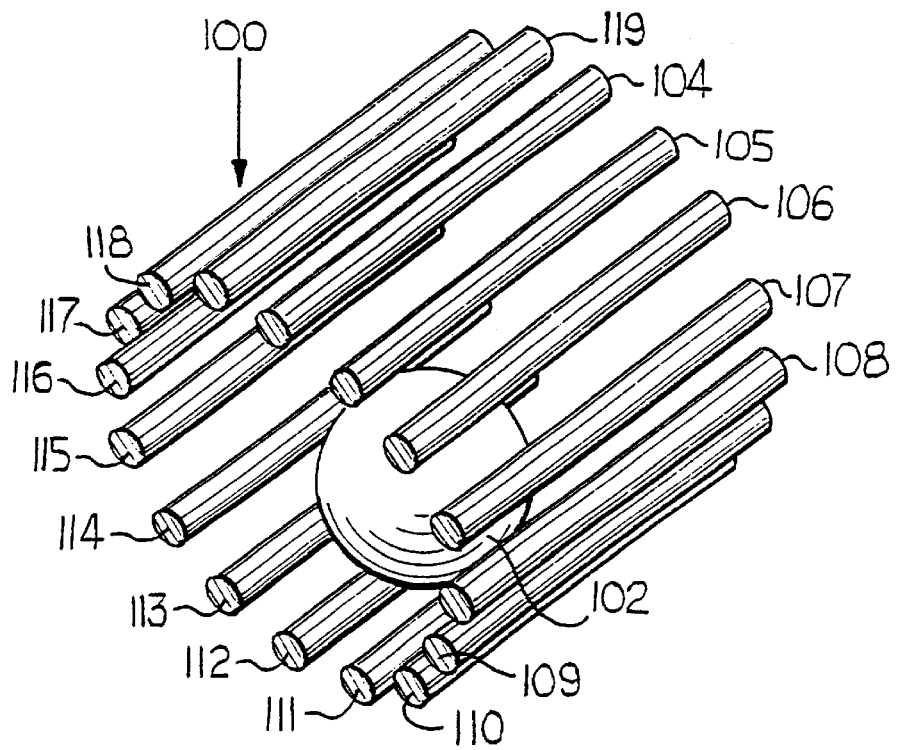
FIG. 10 is a perspective view of the ball and wire cage of another embodiment of the invention.

In another embodiment, the body axis rotation sensor is a wire cage inclinometer 100 as shown in FIG. 10 including a plurality of wires disposed in parallel to the spinal axis of the patient. The wire cage inclinometer 100 includes a conductive sphere 102 surrounded by a circular cage of 16 wires 104–119 disposed in a nonconductive housing. Every other of the wires 104, 106, 108, 110, 112, 114, 116 and 118 are input wires hardwired to eight digital microprocessor inputs 104i, 106i, 108i, 110i, 112i, 114i, 116i and 118i connected to microprocessor 126. Each input wire is also connected to the positive voltage supply (Vcc) via a pull-up resistor. The other wires 105, 107, 109, 111, 113, 115, 117 and 119 are connected to two microprocessor outputs. Output wires 105, 109, 113 and 117 are connected to a first microprocessor output 122 and output wires 107, 111, 115 and 119 are connected to a second microprocessor output 124.

Figure 11:
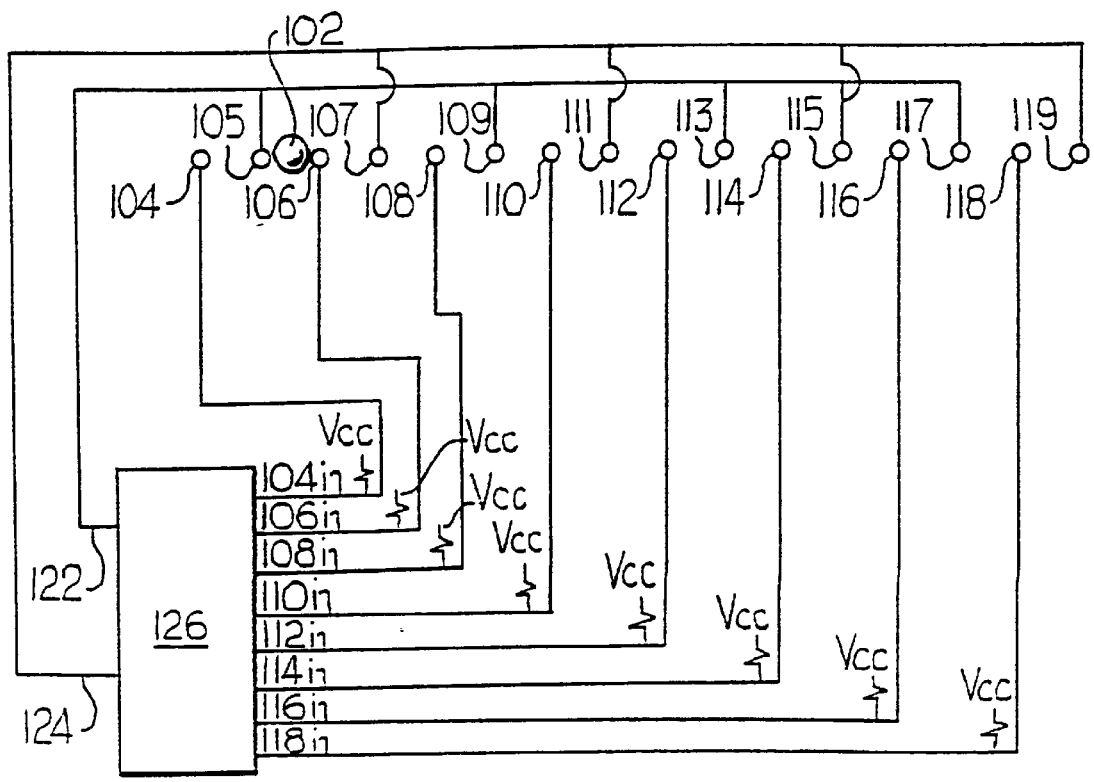
FIG. 11 is a schematic circuit diagram of the ball and wire cage of FIG. 8.

FIG. 11 is a schematic representation of the circuitry of the wire cage accelerometer. The microprocessor periodically enables a digital voltage to the first microprocessor output and then to the second microprocessor output with simultaneous polling of each input wire to check for connection between an input wire and an output wire via the conductive sphere 102. When the patient turns 22.5 degrees, the conductive sphere 102 creates a new short either between the same output wire and a different input wire or between the same input wire and a different output wire. As the patient turns over, the conductive sphere rolls and electrically connects pairs of adjacent output and input wires until coming to a rest in the patient's new position. The patient's final position and the degrees the patient has turned are determined by the location of the connections achieved between adjacent output and input wires. In FIG. 11, the short is schematically shown as occurring between output wire 105 and input wire 106 as an example.

When sixteen detector pins are used as described therein, the body axis position sensor can detect changes in the angular rotation of the patient of at least 22.5 degrees. Sensitivity to greater or lesser changes in the patient's body axis orientation can be achieved by increasing or decreasing the number of detector pins without departing from the present invention.

The present invention has been described with respect to three embodiments which detect the position of a patient's body part relative to the force of gravity. Any inclinometer which detects changes in position relative to the force of gravity may be used without departing from the scope of the invention.

Data from the microprocessor may be used in at least the following ways. As shown in FIGS. 8A and 8B, the data may be relayed to a remote monitor 68 via a radio link (shown in dashed line) or the like at predetermined intervals. The remote monitor displays past turnings or movements which occurred by the spontaneous movement of the patient and/or with the assistance of a nursing staff member. When used as a diagnostic tool, the patient is allowed to turn or move spontaneously with no assistance by a nursing staff member. The data from the patient position monitor displayed on the remote monitor then indicates whether the patient has, without assistance, turned over at least every two hours or has risen from a bed or chair for at least 10 minutes every two hours and thus is not at risk for developing pressure ulcers and does not need a turning intervention program or assistance in movement.

In a related manner, the remote monitor can be used by nursing staff to determine whether the patient was turned or moved a preselected degree, as prescribed, either spontaneously or by a staff member. For patients who occasionally spontaneously turn, move or stand themselves, the remote monitor indicates that the patient accomplished a turning or movement of at least a clinically relevant degree within the past prescribed period and need not be turned or moved again for another prescribed time period by an intervening staff member. The remote monitor may be equipped with a countdown timer set for the prescribed turning interval. The countdown timer automatically resets with each successive turning. An alarm may be activated if the patient has not turned or moved within the prescribed time period or has not turned or moved far enough to relieve tissue pressure.

The data from the microprocessor may also be stored within the patient position monitor itself in a memory subsystem 72 shown in FIGS. 8A and 8B. The memory subsystem 72 may be an EEPROM or RAM. Data stored in the memory subsystem 72 may be read at a later time and is useful for nursing staff quality control documenting compliance with prescribed turning intervention programs.

Thus, the present invention includes a method of monitoring the orientations of the longitudinal body axis of a patient lying down having the steps of: (a) attaching a patient position monitor to the torso or thigh of a patient, the patient position monitor comprising a body axis orientation sensor and a microprocessor which receives output from the body axis orientation sensor; (b) repeatedly measuring the orientation of the body axis of the patient with respect to gravity; and (c) measuring the time spent in the orientation measured in step (b). Changes in the orientation of the patient's body axis may be accomplished by the patient or with assistance from another person. The body axis orientation sensor preferably is one of the above described embodiments thereof.

The present invention further includes a method of preventing pressure ulcers in a bed bound patient including performing the above-described steps of the method of monitoring the orientations of the body axis of a patient further including rotating the body axis of the patient within a prescribed repositioning time period such that the time measured in step (c) is within the prescribed repositioning period.

The present invention also includes a method of monitoring the verticality of a patient having the steps of: (a) attaching a patient position monitor to the thigh of a patient, the patient position monitor comprising a verticality sensor and a microprocessor which receives output from the verticality sensor; (b) repeatedly measuring the orientation of the patient's thigh relative to vertical; and (c) measuring the time spent in the orientation measured in step (b). The verticality sensor employed in this method is the above-described inventive verticality sensor.

The present invention further includes a method of determining compliance with a patient repositioning regimen having the steps of: (a) attaching a patient position monitor to a body part of a patient, the patient position monitor comprising an inclinometer, a microprocessor which receives output from the inclinometer and a recorder which records data from the microprocessor; (b) repeatedly measuring the orientation of the body part of the patient relative to gravity; (c) measuring the time spent in the orientations; (d) recording the measurements of the orientations of the body part of the patient relative to gravity and the time spent in the orientations; and (e) comparing the measurements recorded in step (d) to orientation and time parameters of a prescribed repositioning regimen. An alarm may be sounded when the measurements compared in step (e) do not conform with the parameters of the prescribed repositioning regimen. The method may further include a step of transmitting the measurements recorded in step (d) to a remote receiver which may display the measurements recorded in step (d).

The present invention also includes a method of diagnosing a patient's need for a repositioning regimen comprising the steps of: (a) attaching a patient position monitor to a body part of a patient, the patient position monitor comprising an inclinometer, a microprocessor which receives output from the inclinometer and a recorder which records data from the microprocessor; (b) repeatedly measuring the orientation of the body part of the patient relative to gravity; (c) measuring the time spent in the orientations; (d) recording the measurements of the orientations of the body part of the patient relative to gravity and the time spent in the orientations; and (e) comparing the measurements recorded in step (d) to a set of predetermined minimal repositioning orientation and time parameters.

Turning intervention programs are often coordinated with clothing and bedding changes for incontinent patients. In another embodiment of the invention, input from a humidity wetness and/or fecal material detector is included in the remote monitor. If the bedside monitor indicates that no assisted turning is necessary and no wetness has occurred, then the patient need not unnecessarily be disturbed just to check for wetness. Any suitable wetness detector may be used. One example of a wetness detector is a strip including conductive paths bridged only when body waste decreases the resistance between the paths. Another example is a temperature sensor which sets off an alarm in response to the presence of warm excrement.

Although the present invention may be described in detail in connection with the discussed embodiments, various modifications may be made by one of ordinary skill in the art without departing from the spirit and scope of the present invention. Therefore, the scope of the present invention should be determined by the attached claims.

What is claimed is:

1. A patient position monitor for monitoring the orientation of a part of a patient's body with respect to gravity comprising:

(1) a body axis orientation sensor for repeatedly measuring an arbitrary orientation of a part of a patient's body with respect to gravity; and (2) means for determining the time elapsed between a time when a patient is in one said arbitrary orientation and a time when a patient moves to another said arbitrary orientation based on an output of said body axis orientation sensor, wherein said body axis orientation sensor includes:
   a nonconductive housing;
   a conductive sphere surrounded by a plurality of wires disposed parallel to the body axis of the patient and arranged in a circle within said housing, said wires comprising an even numbered plurality of output wires and a same number of input wires, said output wires each separated by one of said input wires;
   a plurality of input leads connecting each one of said input wires to said determining means; and
   a pair of output leads, every other one of said output wires connected to one of said output leads and the others of said output wires connected to the other of said output leads, wherein said ball is sized to contact one of said output wires and one of said input wires adjacent said one of said output wires such that the contact between the wires is indicative of the orientation of the body axis of the patient relative to gravity.

2. A method of monitoring the orientations of the body axis of a patient lying down comprising the steps of:

(a) attaching a patient position monitor to the torso or thigh of a patient, said patient position monitor comprising a body axis orientation sensor and a microprocessor which receives output from said body axis orientation sensor;

(b) repeatedly measuring an arbitrary orientation of the body axis of the patient with respect to gravity using an accelerometer; and (c) measuring the time elapsed between a time when the patient is in one said arbitrary orientation and a time when the patient moves to another said arbitrary orientation.

3. The method of claim 2 wherein a change in the orientation of the patient's body axis is accomplished by the patient.

4. The method of claim 2 wherein a change in the orientation of the patient's body axis is accomplished with assistance by another person.

5. The method of claim 2 wherein said body axis orientation sensor comprises:

a light impermeable capsule comprising a cylindrical body having a longitudinal axis parallel to the patient's body axis and having a first end portion and a second end portion, said first end portion comprising a circuit board having a radial array of sequentially illuminated light emitting diodes;

a light sensor mounted on said second end portion of said capsule; and a light impermeable sphere disposed in said capsule between said array of light emitting diodes and said light sensor, wherein said sphere is sized to block light emitted from a portion of the light emitting diodes, whereby the detection by said light sensor of light emitted from said light emitting diodes and not blocked by said sphere is indicative of the orientation of the body axis of the patient relative to gravity.

6. A method of preventing pressure ulcers in a bed bound patient comprising performing the method of claim 2 further comprising rotating the body axis of the patient within a prescribed repositioning period such that the time measured in each of step (c) is within said prescribed repositioning period.

7. The method of claim 2, further comprising: monitoring the verticality of the patient by (a) attaching the patient position monitor to the thigh of the patient, said patient position monitor further comprising a verticality sensor, the microprocessor receiving output from said verticality sensor;

(b) repeatedly measuring the orientation of the patient's thigh relative to vertical; and (c) measuring the time spent in said orientation.

8. The method of claim 7 wherein said verticality sensor comprises:

a light impermeable capsule comprising a cylindrical body having a longitudinal axis orthogonal to the patient's body axis disposed medially-laterally to the patient, said cylindrical body further having a first end portion and a second end portion, said second end portion comprising a circuit board having a radial array of sequentially illuminated light emitting diodes;

a light sensor mounted on said second end portion of said capsule; and a light impermeable sphere disposed in said capsule between said array of light emitting diodes and said light sensor, wherein said sphere is sized to block light emitted from a portion of the light emitting diodes, whereby the detection by said light sensor of light emitted from said light emitting diodes and not blocked by said sphere is indicative of the orientation of the patient's thigh relative to vertical.

9. A method for determining compliance with a patient repositioning regimen comprising the steps of:

(a) attaching a patient position monitor to a body part of a patient, said patient position monitor comprising an inclinometer, a microprocessor which receives output from said inclinometer and a recorder which records data from said microprocessor;

(b) repeatedly measuring an arbitrary orientation of the body axis of the patient with respect to gravity using said inclinometer; and (c) measuring the time elapsed between a time when the patient is in one said arbitrary orientation and a time when the patient moves to another said arbitrary orientation;

(d) recording the measurements of the orientations of said body part of the patient relative to gravity and the time spent in said orientations; and (e) comparing the measurements recorded in step (d) to orientation and time parameters of a prescribed repositioning regimen.

10. The method of claim 9 further comprising the step of sounding an alarm when the measurements compared in step (e) do not conform with parameters of said prescribed repositioning regimen.

11. The method of claim 9 further comprising transmitting the measurements recorded in step (d) to a remote receiver.

12. The method of claim 11 wherein said remote receiver displays the measurements recorded in step (d).

13. A method of diagnosing a patient's need for a repositioning regimen comprising the steps of:

(a) attaching a patient position monitor to a body part of a patient, said patient position monitor comprising an inclinometer, a microprocessor which receives output from said inclinometer and a recorder which records data from said microprocessor;

(b) repeatedly measuring an arbitrary orientation of said body part of the patient relative to gravity using said inclinometer; and (c) measuring the time elapsed between a time when the patient is in one said arbitrary orientations and a time when the patient moves to another said arbitrary orientation;

(d) recording the measurements of the orientations of said body part of the patient relative to gravity and the time spent in said orientations; and (e) comparing the measurements recorded in step (d) to a set of predetermined minimal repositioning orientation and time parameters.

* * * * *

UNITED STATES PATENT AND TRADEMARK OFFICE
CERTIFICATE OF CORRECTION

PATENT NO. : 6,129,686
DATED : October 10, 2000
INVENTOR(S) : Mark B. Friedman

It is certified that error appears in the above-identified patent and that said Letters Patent is hereby corrected as shown below:

Column 3 Line 63 "ore" should read --more--.

Column 14 Line 20, Claim 7, after "by" insert colon (:).

Signed and Sealed this

Eighth Day of May, 2001

Attest:

NICHOLAS P. GODICI

Attesting Officer     Acting Director of the United States Patent and Trademark Office